US008609879B2

(12) United States Patent
Teles et al.

(10) Patent No.: US 8,609,879 B2
(45) Date of Patent: Dec. 17, 2013

(54) METHOD FOR THE SEPARATION OF ACETONITRILE FROM WATER

(75) Inventors: Joaquim Henrique Teles, Otterstadt (DE); Hans-Georg Göbbel, Kallstadt (DE); Peter Baßler, Viernheim (DE); Philip Kampe, Lorsch (DE); Kai Gumlich, Mannheim (DE); Christian Bartosch, Mannheim (DE); Ulrich Müller, Neustadt (DE); Richard Jacubinas, Bloomfiled, NJ (US); Natalia Trukhan, Ludwigshafen (DE); Meinolf Weidenbach, Drochtersen (DE); Martin Cogswell, Camlachin (CA)

(73) Assignees: BASF SE, Ludwigshafen (DE); The Dow Chemical Company, Midland, MI (US)

( * ) Notice: Subject to any disclaimer, the term of this patent is extended or adjusted under 35 U.S.C. 154(b) by 417 days.

(21) Appl. No.: 12/837,962

(22) Filed: Jul. 16, 2010

(65) Prior Publication Data
US 2011/0065939 A1 Mar. 17, 2011

Related U.S. Application Data

(60) Provisional application No. 61/226,116, filed on Jul. 16, 2009.

(51) Int. Cl.
C07C 255/00 (2006.01)
(52) U.S. Cl.
USPC .......................................................... 558/435
(58) Field of Classification Search
None
See application file for complete search history.

(56) References Cited

U.S. PATENT DOCUMENTS

| | | | |
|---|---|---|---|
| 5,194,675 | A | 3/1993 | Joerg et al. |
| 6,350,888 | B1 | 2/2002 | Strebelle et al. |
| 7,351,587 | B2 | 4/2008 | Beuermann et al. |
| 2004/0068128 | A1 | 4/2004 | Teles et al. |
| 2007/0043226 | A1 | 2/2007 | Muller et al. |
| 2008/0073201 | A1 | 3/2008 | Van Gysel et al. |
| 2009/0270641 | A1 | 10/2009 | Seo et al. |
| 2010/0197946 | A1 | 8/2010 | Mizuno et al. |

FOREIGN PATENT DOCUMENTS

| | | |
|---|---|---|
| CN | 101397283 | 4/2009 |
| EP | 0 427 062 A2 | 5/1991 |
| EP | 1 580 190 A1 | 9/2005 |
| EP | 1 602 651 A1 | 12/2005 |
| EP | 2 014 654 A1 | 1/2009 |
| WO | WO 01/57009 A1 | 8/2001 |
| WO | WO 2005/044783 A2 | 5/2005 |
| WO | WO 2007/000396 A1 | 1/2007 |
| WO | WO 2009/008493 A2 | 1/2009 |

OTHER PUBLICATIONS

International Search Report issued Dec. 20, 2010, in PCT/EP2010/060310.
K. J. Lissant, "Making and Breaking Emulsions", Res. Lab., Petrolite Corp., St. Louis, Missouri, USA, Chapter 2, 1974, 2 front pages, pp. 111-124.
Spencer E. Taylor, "Resolving Crude Oil Emulsions", Chemistry & Industry, Oct. 19, 1992, 1 front page, pp. 770-773.
Jun Zhang, et al., "Salting-Out assisted liquid/liquid extraction with acetonitrile: a new high throughput sample preparation technique for good laboratory practice bioanalysis using liquid chromatography-mass spectrometry", Biomedical Chromatography, vol. 23, No. 17, XP-002603045, Nov. 17, 2008, pp. 419-425.
Bin Wang, et al. "Sugaring-Out Separation of Acetonitrile from Its Aqueous Solution", Chemical Engineering & Technology, vol. 31, No. 12, 2008, XP-002603046, pp. 1869-1874.
Tingyue Gu, et al., "Phase separation of acetonitrile-water mixture in protein purification", Separations Technology, vol. 4, XP-002603047, Oct. 1994, pp. 258-260.
Manabu Yoshida, et al., "Subzero-Temperature Liquid-Liquid Extraction of Benzodiazepines for High-Performance Liquid Chromatography", Analytical Chemistry, vol. 71, No. 9, XP-002603048, May 1, 1999, pp. 1918-1921.
"HPLC Constant Pressure Pump", May 3, 2008, Retrieved from the Internet: URL:http://www.labhut.com/products/pumps/constant_pressure.php, 2 pages.

*Primary Examiner* — Nyeemah A Grazier
(74) *Attorney, Agent, or Firm* — Oblon, Spivak, McClelland, Maier & Neustadt, L.L.P.

(57) ABSTRACT

A method for separating acetonitrile from water, comprising (i) providing a stream S1 containing at least 95 wt.-%, based on the total weight of S1, acetonitrile and water, wherein the weight ratio of acetonitrile: water is greater than 1; (ii) adding a stream P, comprising at least 95 wt.-% C3, based on the total weight of stream P, to S1 to obtain a mixed stream S2, C3 being propene optionally admixed with propane with a minimum weight ratio of propene: propane of 7:3; (iii) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrile wherein the weight ratio of acetonitrile: water in L2 is less than 1; (iv) separating L1 from L2.

37 Claims, No Drawings

METHOD FOR THE SEPARATION OF ACETONITRILE FROM WATER

The present invention relates to a method for the separation of acetonitrile from water wherein a stream S1 which contains at least 95 wt.-% acetonitrile and water with a weight ratio of acetonitrile:water of greater than 1 is admixed with a stream P which comprises at least 95 wt.-% of C3, C3 either being propene or a mixture of propene with propane, the weight ratio of propene:propane being at least 7:3. The mixed stream is then subjected to temperature and pressure conditions such that two liquid phases are obtained. The first liquid mixture, L1, essentially consists of C3, acetonitrile and water. Preferably, the water content of L1 is 12 wt.-% at most, more preferably in the range of from 1 to 5 wt.-%. The second liquid phase, L2, essentially consists of water and acetonitrile with a weight ratio of acetonitrile:water of greater than 1. Preferably, the C3 content of L2 is 5 wt.-% at most. According to the invention, the two liquid phases L1 and L2 are suitably separated.

According to a preferred embodiment, the present invention relates to a method wherein the stream S1 is obtained from an oxidation process or a downstream workup stage thereof, in particular an epoxidation process or a downstream workup stage thereof, and even more preferably from the epoxidation of propene with hydrogen peroxide in the presence of acetonitrile as solvent or a downstream workup stage thereof. As far as this embodiment is concerned, the present invention is characterized by several possibilities of providing a highly integrated process as far as the recycling of streams obtained during the overall process is concerned. Thus, the present invention in particular relates to a highly integrated process for the production of propylene oxide.

WO 01/57009 A1 relates to a process for the catalytic epoxidation of olefins. From the epoxidation reaction, an exit gas stream is obtained which contains olefin oxide, unreacted olefin and oxygen. This exit gas stream is brought into contact in an absorption unit with the same solvent as used in the reaction stage.

U.S. Pat. No. 6,350,888 B1 relates to a process for making an epoxide, in which process a mixture of reaction products comprising the epoxide, the diluent and water, and possibly also unconverted reactants is obtained. This mixture is contacted with an extraction solvent so as to obtain two distinct liquid phases wherein the extract contains at least some of the extraction solvent and at least 10% of the epoxide produced in the epoxidation reaction.

EP 1 580 190 A1 discloses a method of oxidizing a carbon-carbon double bond of a compound A, which method comprises, as a first step, the oxidation of the carbon-carbon double bond of the compound A using a peroxide as an oxidizing agent in a presence of a titanosilicate catalyst to obtain an oxidation reaction mixture, as a second step, the separation of the compound A from said reaction mixture, and as a third step the returning of the separated compound A to the first step. As particularly preferred compounds A, compounds are disclosed which have at least two or more functional groups with at least one functional group being a carbon-carbon double bond. Especially preferred compounds A are diallyl ether or allyl alcohol. The separation of solvent is only briefly mentioned in EP 1 580 190 A1. Concerning this separation of solvent, example 1 and comparative example 4 of EP 1 580 190 A1 describes the separation via fractional distillation wherein unreacted diallyl ether and methanol are recovered at the top of the distillation column. Recycling of the solvent is not mentioned in EP 1 580 190 A1.

EP 1 602 651 A1 describes a process for producing propylene oxide, wherein the reaction mixture obtained from the epoxidation, containing propylene oxide, consists of two different phases, namely a water layer and an oil layer. These phases are subsequently separated into the water layer and the oil layer. The oil layer contained the organic solvent used in the epoxidation reaction. By separating the reaction mixture into these layers, the propylene oxide contained in the reaction mixture was separated from the water layer into the oil layer. Therefore, EP 1 602 651 A1 is strictly limited to processes wherein the oil layer separated from the water layer primarily contains the organic solvent and the propylene oxide. Although nitriles are generally disclosed as conceivable solvents, acetonitrile is disclosed as solvent which results in a uniform reaction solution which was not separable. In this context, it has to be noted that comparative example 3 of EP 1 602 651 A1 erroneously states that the obtained reaction solution was uniform and separable which should certainly read "uniform and not separable".

EP 2 014 654 A1 describes a method for producing propylene oxide, wherein an vent gas stream which is obtained from the reactor in which the epoxidation reaction is carried, which vent gas stream contains recyclable compounds such as propylene or propylene oxide, is contacted with a solvent containing a nitrile. By absorption in this solvent, the recyclable compounds can be recovered. Further, EP 2 014 654 A1 discloses that, if a mixed solvent such as acetonitrile and water and water is used as solvent in the epoxidation reaction, a portion of the nitrile to be employed in the absorption process can be recovered from the nitrile/water mixture. Explicit methods for recovering said portion of the nitrile solvent, disclosed in EP 2 014 654 A1, are the use of a molecular sieve or zeolite as adsorption agent, or distillation. In FIG. 2, a process is described wherein the solvent recovering encompasses a distillation wherein, at the top of the column, acetonitrile and water are obtained, wherein this gas mixture is subsequently subjected to a pressure swing stage wherefrom water with an acetonitrile content of less than 1 wt.-% and acetonitrile with a water content of less than 1 wt.-% are obtained.

Generally, it was an object of the present invention to provide a novel method for the separation of acetonitrile from water.

It was a further object of the present invention to provide an efficient work-up stage in the production of propylene oxide wherein acetonitrile is used as solvent and hydrogen peroxide is used as oxidizing agent for the epoxidation of propene.

It was a further object of the present invention to provide a highly economical method for the production of propylene oxide wherein acetonitrile is used as solvent and hydrogen peroxide is used as oxidizing agent for the epoxidation or propene.

The present invention relates to a method for separating acetonitrile from water, comprising
(i) providing a stream S1 containing at least 95 wt.-%, based on the total weight of S1, acetonitrile and water, wherein the weight ratio of acetonitrile:water is greater than 1;
(ii) adding a stream P, comprising at least 95 wt.-% C3, based on the total weight of stream P, to S1 to obtain a mixed stream S2, C3 being propene optionally admixed with propane with a minimum weight ratio of propene:propane of 7:3;
(iii) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrile wherein the weight ratio of acetonitrile:water in L2 is less than 1;

(iv) separating L1 from L2.

Generally, it is conceivable to admix a gaseous stream S1 and a gaseous stream P, or a liquid stream S1 and a gaseous stream P, or a gaseous stream S1 and a liquid stream P, or a liquid stream S1 and a liquid stream P. It is preferred that in (ii), a liquid stream P is added to a liquid stream S1.

According to the present invention, at least 95 wt.-% of the stream S1 consist of acetonitrile and water, wherein the weight ratio of acetonitrile:water is greater than 1. Preferably, at least 96 wt.-%, more preferably at least 97 wt.-%, more preferably at least 98 wt.-%, and more preferably at least 99 wt.-% of the stream S1 consist of acetonitrile and water, wherein the weight ratio of acetonitrile:water is greater than 1.

As far as this weight ratio of acetonitrile:water is concerned, preferred ratios are at least 1.5:1, even more preferred ratios at least 2:1. In particular, S1 contains from 60 to 85 wt.-%, preferably from 65 to 80 wt.-%, more preferably from 70 to 80 wt.-% acetonitrile, and from 10 to 35 wt.-%, preferably from 15 to 30 wt.-%, more preferably from 15 to 25 wt.-% water, in each case based on the total weight of S1. Therefore, according to a particularly preferred embodiment of the present invention, at least 99 wt.-% of stream S1 consist of acetonitrile and water, and S1 contains from 70 to 80 wt.-% acetonitrile and from 15 to 25 wt.-% water.

According to a specific embodiment of the present invention, stream S1 comprises at least one glycol, preferably at least one propylene glycol, such as monopropylene glycol, referred to as propylene glycol, and/or dipropylene glycol, and/or tripropylene glycol. In particular, S1 comprises the at least one glycol, preferably the at least one propylene glycol, if S1 is obtained from an epoxidation process wherein propylene is reacted with hydrogen peroxide in the presence of acetonitrile as solvent. Preferably, S1 contains the at least one glycol, preferably the at least one propylene glycol which is preferably selected from the group consisting of propylene glycol, dipropylene glycol, tripropylene glycol, and a mixture of two or three thereof, in an amount of 1 wt.-% or less.

According to (ii), a stream P comprising C3, preferably a liquid stream P, is added to S1. Generally, at least 95 wt.-% of stream P consist of propene or a mixture of propene with propane. If P contains such mixture of propene and propane, the weight ratio of propene:propane will be at least 7:3. Therefore, propene streams can be employed as P or C3 which have varying contents of propane. For example, commercially available propene can be employed as P or C3 which may be either a polymer grade propene or a chemical grade propene. Typically, polymer grade propene will have a propene content of 99 to 99.8 wt.-% and a propane content of 0.2 to 1 wt.-%. Chemical grade propene will typically have a propene content of 92 to 98 wt.-% and a propane content of 2 to 8 wt.-%. According to a preferred embodiment of the present invention, a stream P is employed, at least 95 wt.-% thereof consisting of C3, wherein C3 is a mixture of propene and propane and the content of C3 regarding propene is in the range of from 92 to 98 wt.-%, preferably in the range of from 94 to 97 wt.-%, and the content of C3 regarding propane is in the range of from 2 to 8 wt.-%, preferably in the range of from 3 to 6 wt.-%.

Generally, P is added to S1 in (ii) in an amount so that the weight ratio of C3:acetonitrile in S2 is in the range of from 0.2:1 to 5:1. According to preferred embodiments of the present invention, P is added to S1 in (ii) in an amount so that the weight ratio of C3:acetonitrile in S2 is in the range of from 0.5:1 to 2:1, more preferably in the range of from 1.0:1 to 1.5:1.

According to the present invention, the stream S2 is subjected in (iii) to temperature and pressure conditions so that two liquid phases L1 and L2 are obtained. It was found that it is beneficial for the breakup into these phases L1 and L2 to subject the stream S2 to as low a temperature as possible with the proviso that the temperature is still suitable; for example, the temperature shall not be so low that a solid phase such as ice is formed. Typically, S2 will be brought to a temperature of 92° C. at most. According to the present invention, it is preferred to bring S2 to a temperature in the range of from 5 to 90° C., preferably from 10 to 80° C., more preferably from 15 to 70° C., more preferably from 20 to 60° C., and more preferably from 25 to 45° C. Accordingly, S2 is typically subjected to a pressure of at least 10 bar so that S2 will be present essentially or completely in its liquid form. The term "essentially in its liquid form" as used in this context of the present invention relates to an embodiment according to which at least 95 wt.-%, more preferably at least 99 wt.-% and more preferably at least 99.9 wt.-% of S2 are present in liquid form after being subjected to above-mentioned temperatures and pressures. According to the present invention, it is preferred to subject S2 to a pressure of at least 15 bar, more preferably to a pressure in the range of from 15 to 50 bar, more preferably from 15 to 40 bar, more preferably from 15 to 30 bar, and more preferably from 15 to 25 bar.

Bringing S2 to above-mentioned temperature can be accomplished by any suitable method. According to the present invention, it is preferred to use one or more suitable heat transfer media, e.g. water, in a suitable apparatus, e.g. a shell and tube heat exchanger.

Subjecting S2 to above-mentioned pressure can be accomplished by any suitable method. According to the present invention, it is preferred to use a suitable pump, e.g. a centrifugal pump or a radial pump.

According to the present invention, temperatures and pressures as described above allow for the existence of two distinct liquid phases L1 and L2. According to (iv), the two distinct liquid phases L1 and L2 are suitably separated from each other. Generally, for this separation of the two liquid phases, every conceivable method can be applied. Possible apparatuses used for the separation of L1 from L2 are, for example, gravity settlers, settlers with coalescing aids such as weirs, inclined plates separator, coalescers such as, for example, mats, beds, layers of porous or fibrous solids, or membranes, stagewise mixer-settler equipments, hydrocyclones, centrifuges, suitable columns with or without energy input. Generally, batch mode or continuous mode is conceivable. Preferably, a gravity settler such as vertical or horizontal gravity settler is employed. Still more preferably, a horizontal gravity settler is employed. It was found that due to the considerable density difference and low viscosities achieved for the liquid phases L1 and L2 according to the inventive method, the gravity settler, one of the simplest apparatus, may be employed.

According to one embodiment of the present invention, at least one liquid phase separation improving agent such as at least one suitable anti-emulsifying, demulsifying or emulsion breaking agent can be added. Generally, it is possible to add said liquid phase separation improving agent to S1 in (i) or to S2 in (ii) or to S1 in (i) and to S2 in (ii). The amount of liquid phase separation improving agent added is preferably at most 1 wt.-% based on the total weight of S1 and/or S2. Typically, the amount will be less than 1 wt.-% such as, for example, below 0.5 wt.-% or below 0.1 wt.-%. Suitable agents will be known by the skilled person. Reference is made, e.g., to K. J. Lissant, Making and Breaking Emulsions, Res. Lab., Petrolite Corp., St. Louis, Mo., USA, in: K. J. Lissant (ed.), Emulsion Technology (1974), chapter 2, pp 111-124, Dekker, New York; and to S. E. Taylor, Chem. Ind. (1992), pp 770-773.

According to another embodiment of the present invention, the separation of L1 from L2 is performed without the addition of such additional liquid phase separation improving agent.

From the process of the present invention, a liquid phase L1 is obtained which essentially consists of C3, acetonitrile, and water. The term "essentially consists of C3, acetonitrile and water" as used in this context of the present invention refers to a liquid phase L1 wherein at least 90 wt.-% of L1 consist of C3, acetonitrile and water.

According to a preferred embodiment, at least 95 wt.-%, more preferably at least 98 wt.-% and still more preferably at least 99 wt.-% of L1 consist of the C3, acetonitrile, and water, wherein the water content of L1 is less than 10 wt.-% preferably 9 wt.-% at most, more preferably 5 wt.-% at most, based on the total weight of L1. More preferably, the water content of L1 is in the range of from 1 to 9 wt.-%, more preferably in the range of from 1 to 5 wt.-%, based on the total weight of L1.

Generally, the liquid phase L1 can be used in any suitable process. According to a preferred embodiment of the present invention, the liquid phase L1 may be employed as stream which is passed to an oxidation reaction wherein acetonitrile is used as solvent and wherein propene is oxidized. Still more preferably, the liquid phase L1 may be employed as stream which is passed to an epoxidation reaction wherein acetonitrile is used as solvent and wherein propene is oxidized by hydrogen peroxide to obtain propylene oxide.

According to a preferred embodiment of the present invention, the liquid phase L1, prior to being employed in a suitable process, is subjected to at least one further separation stage. Preferably, this at least one further separation stage serves for separating C3, preferably a portion of C3, from acetonitrile.

A conceivable method is, for example, evaporation of the liquid phase L1 by decompression at a suitable pressure. Preferably, the temperature of the liquid phase is kept essentially constant during decompression. By this decompression, C3 is obtained in gaseous form. Thereafter, it is possible to recycle at least a portion of this gaseous C3 stream, after suitable compression to obtain a liquid stream, as at least a portion of stream P into (ii) of the inventive process.

A preferred method for said separation of C3 from acetonitrile in the at least one further separation stage comprises subjecting the liquid phase L1 to a distillation stage. Preferably, distillation is carried out in a suitable manner so that a stream TL1 is obtained which contains at least 90 wt.-%, preferably at least 95 wt.-% C3, based on the total weight of TL1.

It is also preferred for said separation that a stream BL1 is obtained 95 wt.-%, preferably at least 98 wt.-% of which consist of C3, acetonitrile and water, wherein the C3 content of BL1 is in the range of from 7 to 18 wt.-%, preferably from 10 to 15 wt.-%, in each case based on the total weight of BL1.

Generally, this distillation of L1 can be carried out according to any suitable method. For example, one, two or more distillation towers can be employed provided that above-mentioned streams TL1 and BL1 are obtained. Preferably, in said distillation stage, one distillation tower is employed. More preferably, said distillation is carried out at a dew-point at the top of said distillation tower of at least 40° C., preferably in the range of from 40 to 80° C., more preferably in the range of from 40 to 70° C. Typically, the number of theoretical trays is in the range of from 10 to 20. Typical reflux ratios are in the range of from 0.01 to 0.2 such as, for example, from 0.05 to 0.15.

While it is generally possible to use the liquid phase L1 as such, as described above, it is an especially preferred embodiment of the present invention to subject L1 to above-mentioned separation stage, preferably to above-mentioned distillation stage. It was found that combining the inventive separation of L1 from L2 and the downstream separation of TL1 from BL1 allows for a highly integrated design of the process of the present invention. On the one hand, stream TL1 is especially suitable for being recycled into (ii) of the inventive process as at least a portion of P. If, in addition to at least a portion of TL1, further C3 is added to S1, this further source of C3 may be suitably chosen. For example, additional C3 can be added as fresh propene, for example as chemical grade propene containing about 95 wt.-% propene and about 5 wt.-% propane; certainly, all other suitable sources of additional C3 are conceivable, such as, for example, a C3 stream obtained from a supplier in a Verbund site or the like. Further, it was found that the more C3 is recycled to (ii) via TL1, the more effective the phase separation according to (ii) to (iv) of the inventive process works in terms of as complete a separation of S1 as possible. Therefore, it is preferred that at least a portion of TL1, preferably all of TL1 is recycled into (ii). Moreover, in particular as far as a further preferred embodiment of the present invention is concerned according to which S1 is obtained downstream in an oxidation reaction wherein propene is preferably reacted with hydrogen peroxide in the presence of acetonitrile as solvent, stream BL1 has an ideal composition allowing for direct recycling, without any other intermediate treatment, to the epoxidation reaction.

Further, from the process of the present invention, a liquid phase L2 is obtained which essentially consists of water and acetonitrile wherein the weight ratio of acetonitrile:water in L2 is less than 1. The term "essentially consists of acetonitrile and water" as used in this context of the present invention refers to a liquid phase L2 wherein at least 90 wt.-% of L2 consist of acetonitrile and water.

According to a preferred embodiment, at least 95 wt.-%, more preferably at least 97 wt.-% and still more preferably at least 98 wt.-% of L2 consist of the C3, acetonitrile, and water, wherein the C3 content of L2 is 5 wt.-% at most, preferably 3 wt.-% at most, and more preferably 2 wt.-% at most based on the total weight of L2. As far as the acetonitrile is concerned, the respective content of L2 is preferably less than 45 wt.-%, more preferably in the range of from 10 to 40 wt.-%, more preferably from 10 to 35 wt.%, based on the total weight of L2.

Generally, the liquid phase L2 can be used in any suitable process. For example, it is conceivable that the liquid phase L2 is employed as a stream which is passed to an oxidation reaction or a work-up stage downstream of said oxidation reaction wherein acetonitrile is used as solvent and propene is oxidized, such as an epoxidation reaction wherein acetonitrile is used as solvent and wherein propene is oxidized by hydrogen peroxide to obtain propylene oxide.

According to a preferred embodiment of the present invention, the liquid phase L2, prior to being employed in a suitable process, is subjected to at least one further separation stage. A preferred method for said separation comprises subjecting the liquid phase L2 to a distillation stage. Preferably, distillation is carried out in a suitable manner so that a stream TL2 is obtained which contains from 75 to 95 wt.-%, preferably from 80 to 85 wt.-% acetonitrile, based on the total weight of TL2.

Generally, distillation of L2 can be carried out in one, two, or more distillation towers. If this distillation is carried out in one distillation tower, the dew-point at the top of said distillation tower is typically at least 40° C., preferably in the range of from 40 to 80° C., more preferably in the range of from 40 to 65° C. Typically, the number of theoretical trays is in the range of from 10 to 25. Typical reflux ratios are in the range of from 0.5 to 3. By such process, stream TL2 is obtained as top stream from the distillation tower. The respective bottoms stream, BL2, is preferably essentially free of acetonitrile. In this context, the term "essentially free of acetonitrile" refers to an embodiment according to which the acetonitrile content of BL2 is 500 weight-ppm at most, preferably 300 weight-ppm at most, more preferably 100 weight-ppm at most, based on the total weight of BL2.

Surprisingly, it was found that it is possible to subject liquid phase L2 to an especially designed distillation stage which allows for a highly heat-integrated distillation process. Thus, it was found that separation of L2 is advantageously carried out using a two pressure distillation process, wherein in a first distillation tower, distillation is carried out at a top pressure which is higher than the top pressure of a second distillation tower coupled with said first distillation tower, wherein the condenser used to condense the top stream of the first distillation tower is used simultaneously as the vaporizer of the second distillation tower.

According to this preferred embodiment, liquid stream L2 is preferably introduced in said first distillation tower from which a first bottoms stream and a first top stream are obtained. Preferably, said first distillation tower is operated at conditions which allow for obtaining a vapor top stream VTL2 which contains of from 50 to 70 wt.-%, preferably from 55 to 65 wt.-% of acetonitrile, based on the total weight of VTL2. Typically, said first distillation tower is operated at pressures at the top of the tower in the range of from 10 to 20 bar, preferably from 10 to 15 bar. Generally, the first distillation tower has from 10 to 25, preferably from 15 to 20 theoretical trays. Generally, the reflux ratio of said first distillation tower is in the range of from 0.25 to 2, preferably of from 0.25 to 1. The respective bottoms stream obtained from the first distillation tower is preferably essentially free of acetonitrile. In this context, the term "essentially free of acetonitrile" refers to an embodiment according to which the acetonitrile content of the bottoms stream of the first distillation tower is 500 weight-ppm at most, preferably 300 weight-ppm at most, more preferably 100 weight-ppm at most, based on the total weight of the bottoms stream of the first distillation tower. In the following, said bottoms stream obtained from said first distillation tower, optionally admixed with the bottoms stream obtained from the second distillation tower as described hereinunder, is referred to as stream BL2.

In the context of the two-pressure distillation process, at least a portion of, preferably all of VTL2 is suitably condensed, and this condensed stream is introduced into the second distillation tower from which a second bottoms stream and a second top stream are obtained. Preferably, said second distillation tower is operated at conditions which allow for obtaining a top stream TL2 which contains of from 75 to 95 wt.-%, preferably from 80 to 85 wt.-% of acetonitrile, based on the total weight of TL2. Typically, said second distillation tower is operated at pressures at the top of the tower in the range of from 1 to 5 bar, preferably from 1 to 2 bar. Generally, the second distillation tower has from 8 to 20, preferably from 10 to 15 theoretical trays. Generally, the reflux ratio of said second distillation tower is in the range of from 0.5 to 5, preferably of from 1 to 3. The respective bottoms stream obtained from the second distillation tower is preferably essentially free of acetonitrile. In this context, the term "essentially free of acetonitrile" refers to an embodiment according to which the acetonitrile content of the bottoms stream of the second distillation tower is 500 weight-ppm at most, preferably 300 weight-ppm at most, more preferably 100 weight-ppm at most, based on the total weight of the bottoms stream of the second distillation tower.

Preferably, TL2 obtained from the respective distillation tower is at least partially, preferably completely recycled into the inventive process. More preferably, TL2 is either combined with S1 or with S2 or with P.

If stream S1 contains the at least one propylene glycol, as described above, the stream BL2 obtained from said distillation preferably contains the at least one propylene glycol in an amount of from 1 to 5 wt.-%, more preferably in an amount of from 2 to 5 wt.-%, based on the total weight of BL2, whereas stream TL2 is essentially free of the at least one propylene glycol. In this context of the present invention, the term "TL2 is essentially free of the at least one propylene glycol" refers to an embodiment according to which the content of TL2 as to the at least one propylene glycol is 500 weight-ppm at most TL2 is essentially free of the at least one propylene glycol, preferably 200 weight-ppm at most.

If BL2 contains no or essentially no propylene glycol, it is preferred to pass BL2 directly to a suitable waste water treatment plant such as, e.g. a biological waste water treatment plant. It was found that no specific treatment for the waste water produced by the inventive process is required, rendering the process even more cost-efficient and environment-friendly.

If BL2 contains the at least one propylene glycol in significant amounts, such as in an amount of from 1 to 5 wt.-%, more preferably in an amount of from 2 to 5 wt.-%, based on the total weight of BL2, it can be a preferred embodiment of the present invention to pass BL2 to a suitable propylene glycol separation stage wherein the at least one propylene glycol is suitably separated from water and/or wherein two or more different propylene glycols are separate from each other. This process for the separation of the at least one propylene glycol from BL2 can be carried out, for example, by evaporating the mixture in at least two, preferably three evaporation and/or distillation stages, preferably three evaporation stages, at decreasing operating pressures, preferably in the ranges of 1.5 to 5.5 bar at a temperature of 111 to 155° C., followed by 1.3 to 5.0 bar at a temperature of 107 to 152° C., followed in turn by 0.7 to 4.0 bar at a temperature of 90 to 144° C., thus obtaining mixture BL2' and mixture BL2"; and separating the mixture BL2' in at least one further distillation step, obtaining a mixture BL2-I comprising at least 70 wt.-% of water and a mixture BL2-II comprising less than 30 wt.-% of water. It is especially preferred to further separate mixture BL2" into a mixture BL2-Ia comprising at least 90 wt.-% of water and a mixture BL2-Ib comprising less than 95 wt.-% of water by means of reverse osmosis. According to a preferred embodiment, the at least one propylene glycol is separated from the mixture BL2-II, preferably admixed with mixture BL2-Ib, in at least one further distillation step. According to a still further preferred embodiment, mixtures BL2" and BL2-I are combined and further separated into mixture BL2-Ia comprising at least 90 wt.-% of water and mixture BL2-Ib comprising less than 95 wt.-% of water by means of reverse osmosis.

Therefore, the present invention also relates to a method as described above wherein (aa) L2 is introduced into the first distillation tower from which a vapor top stream VTL2 is obtained containing from 50 to 70 wt.-% acetonitrile, based on the total weight of top stream VTL2, the distillation preferably being carried out at a top pressure of from 10 to 20 bar; and
(bb) at least partially condensing VTL2 obtained in (aa) and introducing the condensed stream into the second distillation tower wherefrom TL2 is obtained as top stream, the distillation preferably being carried out at a top pressure of from 1 to 5 bar,
wherein the condenser used to condense VTL2 is simultaneously used as vaporizer of the second distillation tower.

It was surprisingly found that this concept wherein most of the water is separated under pressure in a first tower and wherein a comparatively small stream is distilled at lower pressures. In total, this concept leads to a lesser energy demand of the separation problem.

According to a preferred embodiment of the present invention, stream S1 subjected to the process of the present invention is provided by an oxidation process or a down-stream workup stage thereof. More preferably, stream S1 is obtained from an epoxidation process or a downstream workup stage thereof. More preferably, stream S1 is obtained from the epoxidation of propene or a workup stage thereof. More preferably, stream S1 is obtained from the epoxidation of propene wherein hydrogen peroxide is used as oxidizing agent, or a workup stage thereof. Even more preferably, stream S1 is obtained from the epoxidation of propene in the presence of acetonitrile as a solvent wherein hydrogen peroxide is used as oxidizing agent, or a downstream workup stage thereof. Most preferably, stream S1 is obtained from a workup stage of the epoxidation of propene in the presence of acetonitrile as a solvent wherein hydrogen peroxide is used as oxidizing agent. Therefore, according to these preferred embodiments, the method for separating acetonitrile from water, as described hereinabove, can be seen as a specific workup stage of said oxidation process, in particular of said epoxidation process. Therefore, the present invention also relates to an oxidation process, preferably an epoxidation process, more preferably a process for the production of propylene oxide, more preferably a process for the production of propylene oxide in the presence of acetonitrile as solvent, more preferably a process for the production of propylene oxide wherein propene is reacted with hydrogen peroxide in the presence of acetonitrile as solvent, still more preferably a highly integrated process for the production of propylene oxide wherein propene is reacted with hydrogen peroxide in the presence of acetonitrile as solvent, said process comprising above-described method for separating acetonitrile from water or any preferred embodiment of this method for separating acetonitrile from water.

According to a preferred embodiment, in said epoxidation process, propene is reacted with hydrogen peroxide in a reaction apparatus in the presence of acetonitrile as solvent, wherefrom a stream S0 is obtained leaving the reaction apparatus, S0 containing acetonitrile, water, propylene oxide, and optionally non-reacted propene, oxygen, and further optionally propane. In particular, stream S0 contains propane if propene used as starting material for the epoxidation reaction is contained in a mixture which, in addition to propene, also contains propane. If such mixture of propene and propane is used as stream subjected to epoxidation, the weight ratio of propene:propane will be at least 7:3. For example, commercially available propene can be employed as which may be either a polymer grade propene or a chemical grade propene. Typically, polymer grade propene will have a propene content of 99 to 99.8 wt.-% and a propane content of 0.2 to 1 wt.-%. Chemical grade propene will typically have a propene content of 92 to 98 wt.-% and a propane content of 2 to 8 wt.-%. According to a preferred embodiment of the present invention, a mixture of propene and propane is subjected to epoxidation which has a propene content in the range of from 92 to 98 wt.-%, preferably in the range of from 94 to 97 wt.-%, and a propane content in the range of from 2 to 8 wt.-%, preferably in the range of from 3 to 6 wt.-%.

Therefore, the present invention also relates to the method as described above, wherein according to (i), S1 is provided by a process comprising
(a) reacting propene, optionally admixed with propane, with hydrogen peroxide in a reaction apparatus in the presence of acetonitrile as solvent, obtaining a stream S0 leaving the reaction apparatus, S0 containing acetonitrile, water, propylene oxide, and optionally non-reacted propene, oxygen, and further optionally propane.

According to a preferred embodiment of the present invention, the reaction in (a) is carried out in the presence of at least one suitable catalyst, preferably in the presence of at least one suitable heterogeneous catalyst. Even more preferably, the at least one suitable catalyst comprises at least one zeolite. Specific mention may be made of titanium-, germanium-, tellurium-, vanadium-, chromium-, niobium-, zirconium-containing zeolites having a pentasil zeolite structure, in particular the types which can be assigned by X-ray-crystallography to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG and ZON, and mixed structures of two or more of the abovementioned structures. For the purposes of the present invention, preference is given to using Ti zeolites having an MFI structure, an MEL structure, an MFI/MEL mixed structure or an MWW structure. Particular preference is given to using zeolite catalysts of the Ti-MWW structure. The catalysts, especially preferably the titanium zeolite catalysts and still more preferably the catalysts having Ti-MWW structure, can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. The preparation of such preferred catalysts is described, e.g., in US2007043226 A1, in particular in Examples 3 and 5 of US2007043226 A1.

Generally, the reaction in (a) can be carried out in any appropriate way. Thus, for example, it can be carried out in a batch reactor or in at least one semi-continuously operated reactor or in at least one continuously operated reactor. Particularly, the continuous mode of operation is preferred. In this particularly preferred embodiment, the reaction is preferably carried out at from −10 to 120° C., more preferably from 30 to 90° C. and particularly preferably from 30 to 65° C. Typically, the temperature at which the reaction is carried out is not kept constant but continuously or step-wise adjusted to allow for a constant hydrogen peroxide conversion as determined in stream S0 leaving the reactor in which the epoxidation is carried out. If the epoxidation is carried out in a at least one continuously operated reactor such as a tube reactor or a tube bundle reactor which contains at least one cooling jacket surrounding the at least one tube, the term "reaction temperature" as used herein refers to the temperature of the cooling medium when entering the cooling jacket. Generally, due to catalyst deactivation, the reaction temperature is continuously or step-wise increased. Typically, the reaction temperature is continuously or step-wise increased of by 1° C./day at most. Preferred hydrogen peroxide conversion is at least 80%, more preferably at least 85%. The principle of a preferred hydrogen peroxide conversion determination is described in U.S. Pat. No. 7,351,587 B2, in particular in Examples 1, 2 and 3 of U.S. Pat. No. 7,351,587 B2. The pressures in the at least one reactor are generally in the range from 3 to 100 bar, preferably from 15 to 45 bar. In particularly preferred embodiments of the process of the present invention, the reaction is carried out at temperatures and pressures at which the reaction mixture is liquid and no gas phase is present in the at least one reactor. The molar ratio of propene:hydrogen peroxide with regard to the starting materials passed into the at least one reactor in which epoxidation is carried is typically in the range of from 0.9:1 to 3.0:1, with a range of from 0.98:1 to 1.6:1 being preferred and a range of from 1.0 to 1.5 being especially preferred. The amount of acetonitrile passed to the at least one reactor is adjusted so that the hydrogen peroxide concentration of the overall stream passed to the at least one reactor in which the epoxidation is carried out is typically in the range of from 2 to 20 wt.-%, preferably from 5 to 12 wt.-%, based on the total weight of the overall stream.

According to especially preferred embodiments according to the present invention, the overall stream passed to the at least one epoxidation reactor. i.e. the reactor feed, contains of from 50 to 80, preferably from 60 to 70 wt.-% acetonitrile, of from 7 to 14, preferably from 8 to 11 wt.-% propene, of from 5 to 12, preferably from 6 to 10 wt.-% hydrogen peroxide, and of from 10 to 25, preferably from 12 to 20 M.-% water.

In a likewise preferred embodiment of the process of the present invention, the reaction of the propene can be carried out in two or more stages. A two-stage reaction takes place, for example, as follows:
(A) propene, optionally admixed with propane, is reacted with hydrogen peroxide in the presence of acetonitrile as solvent to give a mixture comprising propylene oxide, oxygen, and unreacted hydrogen peroxide, and optionally propane;
(B) the unreacted hydrogen peroxide is separated off from the mixture resulting from (A);
(C) the hydrogen peroxide which has been separated off according to (B) is reacted with propene, optionally admixed with propane.

As far as the preferred epoxidation reaction conditions of stage (A) are concerned, reference is made to the preferred epoxidation reaction as discussed above. The hydrogen peroxide can be separated off according to (B) by any suitable methods. The hydrogen peroxide is preferably separated off by distillation using one or more distillation towers, preferably one distillation tower. This distillation tower is preferably operated at conditions allowing for obtaining a top stream which contains hydrogen peroxide in an amount of 100 weight-ppm at most, based on the total weight of the top stream, preferably containing essentially no hydrogen peroxide. Additionally this distillation tower is preferably operated at conditions allowing for obtaining a top stream which contains at least 80%, preferably at least 90% and most preferably at least 95% of the propylene oxide contained in the feed. Typically, this distillation tower has of from 15 to 45, preferably from 20 to 40 theoretical trays and is operated at a pressure at the top of the tower in a range of from 0.5 to 1.2 bar, preferably from 0.7 to 1.1 bar. The reflux ratio of this distillation tower is typically in the range of from 0.05 to 0.5, preferably from 0.1 to 0.2. The bottoms stream obtained from the distillation tower in (B), containing essentially all of the unreacted hydrogen peroxide from (A) and further containing acetonitrile, water and optionally at least one propylene glycol, is passed to stage (C). As far as stage (C) is concerned, it is preferred to use an adiabatic reactor, preferably an adiabatic shaft reactor. Epoxidation conditions in (C) are preferred allowing for a hydrogen peroxide conversion at the outlet of (C) of at least 99%, preferably at least 99.5% based on the hydrogen peroxide fed to (A). In (C), it is preferred to use the same catalyst as in (A). As far as the propene is concerned which is introduced into the reactor used in (C), reference is made to the propene already discussed hereinabove in the context of (a). Thus, for example, chemical grade propene or polymer grade propene can be used, with chemical grade propene being preferred. If stages (A) and (C) are used in the present invention, the reactors are preferably operated so that the overall propene conversion, taking into account conversion in (A) and conversion in (C), is at least 80%, more preferably at least 85%.

As described hereinabove, a preferred embodiment of the present invention includes separating acetonitrile from C3 in at least one further separation stage by subjecting the liquid phase L1 to a distillation stage wherefrom a stream TL1 is obtained which contains at least 90 wt.-%, preferably at least 95 wt.-% C3, based on the total weight of TL1 and wherefrom a stream BL1 is obtained 95 wt.-%, preferably at least 98 wt.-% of which consist of C3, acetonitrile and water, wherein the C3 content of BL1 is in the range of from 7 to 18 wt.-%, preferably from 10 to 15 wt.-%, in each case based on the total weight of BL1. Surprisingly, it was found that BL1 thus obtained can be recycled into the epoxidation process, most preferably without any intermediate workup of BL1, due to the preferred composition of the overall stream passed into the at least one epoxidation reactor and the preferred composition of BL1. Therefore, according to a preferred embodiment, at least a portion of BL1 as described hereinabove is recycled into (a). Therefore, the preferred inventive method for separating acetonitrile from water allows for an integrated epoxidation process including the economic advantages of reusing the epoxidation solvent acetonitrile separated from water in the workup stages and, further, suitably making use of propene employed for said separation of the solvent acetonitrile from water.

Generally, it is conceivable that, apart from BL1, additional fresh acetonitrile is needed. This may be due to losses of acetonitrile throughout the overall process. As additional acetonitrile, pure or essentially pure acetonitrile may be added, e.g. to the stream BL1 and/or at other suitable point or points upstream the reactor inlet. It is also conceivable to add crude acetonitrile such as an azeotrope of acetonitrile and water, probably also containing impurities, wherein such crude acetonitrile is typically obtainable, for example, by the acrylonitrile process. In this latter case, it would be preferred to add the acetonitrile, namely the crude acetonitrile, upstream the phase separation.

According to a preferred embodiment of the present invention, the stream S0 obtained from (a), in particular S0 consisting of the top stream obtained from the distillation tower used in (B) combined with the reactor effluent obtained from (C), is passed to a suitable downstream workup stage. Preferably, in this downstream workup stage, propene, oxygen, and propane are separated from S0 to obtain a stream essentially consisting of acetonitrile, water, and propylene oxide. This workup stage is referred to as stage (b) in the context of the present invention.

Separation according to stage (b) can be conducted by every suitable method. Most preferably, separation is conducted by distillation. Separation according to stage (b) is preferably carried out in at least one distillation tower, more preferably in one distillation tower. Preferably, this column has of from 10 to 30, more preferably of from 15 to 25 theoretical trays. The distillation tower is preferably operated at a top pressure of from 0.5 to 1.2 bar, more preferably of from 0.7 to 1.1 bar.

In order to facilitate said separation task, it was found that it is advantageous to add either acetonitrile or a mixture of acetonitrile with water to the top of the column. It is believed that this external reflux serves as stripping agent which, among others, prevents propylene oxide from being separated via the top of the distillation tower. According to a preferred embodiment of the present invention, a portion of the bottom stream of the distillation tower employed in stage (c) is used. It is also conceivable that stream TL2 or a portion thereof is used as stripping agent. Typically, the amount of TL2 will not be sufficient, and another stream will be added. Typically, the weight ratio of the amount of acetonitrile fed as external reflux to the top of the distillation tower:weight of the stream S0 fed into and to be separated in the distillation tower is in the range of from 1:1 to 4:1 preferably from 1.5:1 to 3:1. The temperature of the external reflux is generally in the range of from 2 to 20° C., preferably in the range of from 5 to 15° C.

According to the present invention, at least 95 vol.-%, preferably at least 90 vol.-% and still more preferably at least 70 vol.-% of the top stream of the distillation column according to (b) consist of propene, oxygen, and optionally propane. Depending on its oxygen content, this top stream can be passed to a further suitable workup stage wherein the oxygen content is suitably decreased in order to allow, e.g., for recycling the oxygen-depleted stream to be recycled to one or more stages of the present invention, such as a starting material for stage (a) of the inventive process like stage (A) or stage (C), or as portion of stream P. If the oxygen content of said top stream is reduced, it is preferred to reduce the oxygen by reaction with hydrogen in the presence of a suitable catalyst. Such catalysts are, for example, catalysts comprising tin and at least one noble metal as described in WO 2007/000396 A1, in particular in Example 1 of WO 2007/000396 A1. It is also conceivable to use catalysts comprising copper in elemental and/or oxidic form on a support, wherein copper is present on the support in an amount of 30 to 80 wt.-% based on the whole catalyst and calculated as CuO. Such catalysts can be prepared, for example, according to the example of EP 0 427 062 A2, catalyst 2, page 4, lines 41 to 50 (corresponding to U.S. Pat. No. 5,194,675). However, in order to reduce the oxygen content, also other suitable methods are conceivable. Optionally, said top stream, prior to be subjected to hydrogenation, can be compressed and partially condensed wherein a liquid stream is obtained which essentially consists of C3 and acetonitrile and which contains minor amounts of water. The non-condensed portion essentially consists of C3 and oxygen and contains a minor amount of water wherein, compared to the basic stream, the oxygen content is increased while still being in a range so that the mixture is not ignitable. This oxygen-enriched is then subjected to hydrogenation.

Further according to the present invention, at least 98 wt.-%, preferably at least 98.5 wt.-% and still more preferably at least 99 wt.-% of the bottoms stream of the distillation column according to (b) consist of propylene oxide, acetonitrile, water, and optionally at least one propylene glycol. Prior to feeding this bottoms stream as stream S1 to the method according to the present invention, it is especially preferred to separate propylene oxide from said bottoms stream according to a stage (c) of the inventive process in order to obtain a stream which is essentially free of propylene oxide, which stream can be partially used as stripping agent for stage (b).

Separation according to stage (c) can be conducted by every suitable method. Most preferably, separation is conducted by distillation. Separation according to stage (c) is preferably carried out in at least one distillation tower, more preferably in one distillation tower. Preferably, this tower has of from 50 to 80, more preferably of from 60 to 70 theoretical trays. The distillation tower is preferably operated at a top pressure of from 0.2 to 2 bar, more preferably of from 0.4 to 1 bar. Preferably, at least one suitable polar solvent such as preferably water is added in the upper part of the column as extractive agent. According to a preferred embodiment, separation according to stage (c) can be carried out by

- introducing said bottoms stream into an extractive distillation column;
- additionally introducing a polar extracting solvent into said extractive distillation column;
- distilling propylene oxide overhead from said extractive distillation column as top stream, the top stream comprising only minor amounts of acetonitrile such as 500 ppm or less;
- compressing the top stream obtained overhead in the previous step by means of at least one compressor to give a compressed vapor,
- condensing the compressed vapor obtained in in the previous step and returning at least part of the heat of condensation to at least one reboiler employed in the extractive distillation column.

From this distillation tower according to (c), a top stream is obtained which contains at least 90 wt.-%, preferably at least 95 wt.-% of propylene oxide. Depending on the requirements on the propylene oxide quality, it is conceivable to use this propylene oxide fraction without any further purification. It is, however, also conceivable to further purify said propylene oxide fraction, for example in at least one further distillation stage. From such further distillation stage, a propylene oxide stream may be obtained wherein at least 99.5 wt.-%, more preferably at least 99.9 wt.-% of said stream consist of propylene oxide.

Further from this distillation tower according to (c), a bottoms stream is obtained which typically contains 500 weight-ppm at most, preferably 100 weight-ppm at most, and more preferably 60 weight-ppm at most of propylene oxide, based on the weight of the bottoms stream. In particular, at least 98 wt.-%, more preferably at least 98.5 wt.-% and more preferably at least 99 wt.-% of the bottoms stream consist of acetonitrile, water, and optionally at least one propylene glycol.

Depending on the specific conditions during the upstream stages of the present invention, i.e. stages (a), optionally (b), and/or (c), this bottoms stream obtained from the distillation tower according to (c) may also contain certain amounts of hydroperoxides such as certain amounts of hydrogen peroxide and/or certain amounts of organic hydroperoxides, for example, 1-hydroperoxypropanol-2 and/or 2-hydroperoxypropanol-1. Typically, the bottoms stream obtained from the distillation tower according to (c) may contain up to 2 wt.-%, preferably up to 1 wt.-% of these hydroperoxides in total, based on the weight of the bottoms stream. In order to reduce the hydroperoxide content and, thus, to avoid the build-up of the hydroperoxides which are believed to have a detrimental influence as far as the formation of undesirable by-products and safety aspects based on the decomposition of the hydroperoxides are concerned, it is preferred to subject the bottoms stream obtained from the distillation tower according to (c) to at least one further process stage. Said build-up especially occurs if the inventive highly integrated process is realized. While every suitable method for at least partially removing these hydroperoxides is conceivable, it is especially preferred to catalytically reduce, preferably to catalytically hydrogenate the hydroperoxides. As suitably catalyst, a catalyst may be mentioned which is described in US 20040068128 A1, in particular in paragraphs [0053] to [0076]. Preferred catalysts are selected from the group consisting of heterogeneous catalysts comprising Ru, Ni, Pd, Pt, either individually or as a mixture of two or more thereof, as active metal on a suitable support material. An especially suitable catalyst, namely a supported catalyst comprising 5% by weight of Pd on activated carbon is, described in Example E2 of US 20040068128 A1. The pressure during hydrogenation is typically in the range of from 1 to 100 bar(abs), preferably from 1 to 10 bar(abs), and the temperature during hydrogenation is typically in the range of from 0 to 180° C., preferably from 25 to 120° C., more preferably from 65 to 85° C. The hydrogen partial pressure during hydrogenation is preferably in the range of from more than 1 to 20 bar, more preferably from 2 to 15 bar and still more preferably from 3 to 13 bar. If the hydrogenation is carried out in a fixed bed, which is preferred, the residence time of the liquid passed through the hydrogenation reactor is generally in the range of from 1 second (s) to 1 hour (h), preferably from 10 s to 20 minutes (min), in particular from 30 to 5 min.

Depending on the reaction conditions employed for reducing, preferably hydrogenating the bottoms stream obtained from the distillation tower according to (c), it may be necessary to the separate the resulting stream from the catalyst, preferably hydrogenation catalyst and/or non-reacted reducing agent, preferably hydrogen and/or by-products from the hydrogenation, preferably CO and/or methane.

In particular, the stream resulting from reduction, preferably hydrogenation, contains at least 95 wt.-% acetonitrile and water, based on the total weight of the bottoms stream, wherein the weight ratio of acetonitrile:water is greater than 1. Generally, it is conceivable to use the bottoms stream obtained from the distillation tower according to (c) as stream S1 of the present invention.

Depending on the specific conditions during the upstream stages of the present invention, i.e. stages (a), optionally (b), and/or (c) and/or the reduction, preferably the hydrogenation stage, the stream obtained from reduction, preferably hydrogenation may contain certain amounts of acetaldehyde and optionally further low boilers such as, for example, propionaldehyde and acetone. Typically, this stream may contain up to 2000 weight-ppm, preferably up to 1000 weight-ppm, more preferably up to 300 weight-ppm of acetaldehyde and other lowboilers in total, based on the total weight of this stream. In order to reduce the acetaldehyde content and optionally the content with respect to the other low boilers and, thus, to avoid the build-up of these compounds which especially occurs if the inventive highly integrated process is realized, it is preferred to subject this stream to at least one further process stage. While every suitable method for at least partially removing acetaldehyde is conceivable, it is especially preferred to separate acetaldehyde from the stream by distillation. Separation according to this stage is preferably carried out in at least one distillation tower, more preferably in one distillation tower. Preferably, this tower has of from 15 to 40, more preferably of from 15 to 30 theoretical trays. The distillation tower is preferably operated at a top pressure of from 0.7 to 2 bar, more preferably of from 1.1 to 1.5 bar.

From this distillation tower, a bottoms stream is obtained which typically contains 200 weight-ppm at most, preferably 100 weight-ppm at most, and more preferably 50 weight-ppm at most of acetaldehyde, other low boilers as described above, in total, based on the weight of the bottoms stream. In particular, at least 99 wt.-%, more preferably at least 99.5 wt.-% and more preferably at least 99.7 wt.-% of the bottoms stream consist of acetonitrile, water, and optionally at least one propylene glycol. In particular, the bottoms stream contains at least 95 wt.-% acetonitrile and water, based on the total weight of the bottoms stream, wherein the weight ratio of acetonitrile:water is greater than 1. Preferably, this bottoms stream is used as stream 51 in the process of the present invention. According to a conceivable embodiment of the present invention, no such distillation stage is needed.

Therefore, the present invention also relates to the method as described above, further comprising (y) subjecting the stream obtained from (c) to a hydrogenation stage, preferably to a catalytical hydrogenation stage, the catalyst preferably being a heterogeneous catalysts comprising Ru, Ni, Pd, Pt, either individually or as a mixture of two or more thereof, as active metal on a suitable support material, in particular Pd on activated carbon; said hydrogenation preferably being carried out at a pressure during hydrogenation in the range of from 1 to 100 bar(abs), preferably from 1 to 10 bar(abs), and a temperature during hydrogenation in the range of from 0 to 180° C., preferably from 25 to 120° C., more preferably from 65 to 85° C.;

(z) subjecting the stream obtained from (y) to a distillation stage, preferably carried out in a distillation column operated at a top pressure of from 0.7 to 2 bar, more preferably of from 1.1 to 1.5 bar, to obtained stream S1 and subjecting S1 to step (d) as discussed hereinunder.

Generally, the present invention relates to the method as described above, wherein according to (i), S1 is provided by a process comprising (a) reacting propene with hydrogen peroxide in a reaction apparatus in the presence of acetonitrile as solvent, obtaining a stream S0 leaving the reaction apparatus, S0 containing acetonitrile, water, propylene oxide, and optionally non-reacted propene, oxygen, and further optionally propane;

(b) optionally separating propene, oxygen, and propane from S0 to obtain a stream essentially consisting of acetonitrile, water, and propylene oxide;

(c) separating propylene oxide from S0 or the stream obtained from (b), thus obtaining stream S1.

As described hereinabove, the inventive method of separating acetonitrile from water is preferably integrated as workup stage in a process for the preparation of propylene oxide. Especially as part of this epoxidation process, the inventive method allows for a highly integrated process. Therefore, the present invention also relates to a highly integrated process for the preparation of propylene oxide, the process comprising (a) reacting propene, optionally admixed with propane, with hydrogen peroxide in a reaction apparatus in the presence of acetonitrile as solvent, obtaining a stream S0 leaving said reaction apparatus, S0 containing acetonitrile, water, propylene oxide, and optionally non-reacted propene, oxygen, and optionally propane;

(b) optionally separating propene, optionally together with propane, and oxygen from S0 to obtain a stream, at least 99 wt.-% thereof consisting of acetonitrile, water, and propylene oxide;

(c) separating propylene oxide from S0 or the stream obtained from (b), thus obtaining a stream S1 containing at least 95 wt.-% acetonitrile and water, based on the total weight of S1, wherein the weight ratio of acetonitrile:water is greater than 1, (d) adding a stream P, comprising at least 95 wt.-% C3, based on the total weight of stream P, to S1 to obtain a mixed stream S2, C3 being propene optionally admixed with propane with a minimum weight ratio of propene:propane of 7:3;

(e) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrite wherein the weight ratio of acetonitrile:water in L2 is less than 1;

(f) separating L1 from L2;

(g) subjecting L1 to a distillation stage wherefrom a stream TL1 is obtained which contains at least 90 wt.-% C3, based on the total weight of TL1; and wherefrom a further stream BL1 is obtained, at least 95 wt.-% of BL1 consisting of C3, acetonitrile and water, wherein the C3 content of BL1 is in the range of from 7 to 18 wt.-% based on the total weight of BL1;

(h) subjecting L2 to a distillation stage wherefrom a stream TL2 is obtained which contains from 75 to 95 wt.-%, preferably from 80 to 85 wt.-% acetonitrile, based on the total weight of TL2;

wherein at least a portion of stream BL1 is recycled into (a); and/or wherein at least a portion of TL1 is recycled into (d); and/or wherein at least a portion of TL2 is recycled into (d).

It is especially preferred to recycle BL1 into (a) and TL1 into (d) and TL2 into (d).

Above-described process stages, including stages (y) and (z), may be carried out either in continuous mode, in semi-continuous mode or in batch mode. Preferably, all stages are carried out in continuous mode.

As far as preferred compositions of said streams, preferred reaction conditions, preferred separation conditions, preferred distillation conditions, or the like, and further preferred embodiments as far, for example, preferred and/or optional additional intermediate and/or workup stages are concerned, reference is made to the respective disclosure hereinabove.

The present invention is further illustrated in the following examples.

EXAMPLES

Example 1

Epoxidation of Propene

The epoxidation was performed in a continuous tubular reactor having a cooling jacket and a catalytic bed. The reactor had a length of 1440 mm and an inner diameter of 7 mm and was built of stainless steel (specification 1.4571). The reaction tube was surrounded by a cooling jacket through which a cooling medium (water/glycol mixture) was circulated. The reactor was operated in an up-flow mode. Suitable thermoelements were located just above and below the catalytic bed axially centered in the tube in order to measure the catalytic bed entry and exit temperatures. The reactor was operated at a constant pressure of 20 bar by using a pressure regulating valve at the reactor exit. The temperature was controlled by circulating the cooling medium (fluid) in the reactor mantle in concurrent mode relative to the product. The cooling medium entrance temperature is measured by a thermoelement and used to regulate the thermostat. This temperature is referred to as the "reaction temperature" and was held constant at 63° C. throughout the experiment. The flow rate of the cooling medium is adjusted so that the exit temperature of the cooling medium is no more than 1° C. above the cooling medium entrance temperature.

The reactor was the filled from below with a layer of glass beads (80 mm), then with the catalyst and any remaining room was filled up with glass beads. As catalyst, 15 g of a catalyst were used which were produced by mixing 100 parts of a Ti-MWW powder containing 1.5 wt.-% of Ti with 40 parts of pyrogenic silica and with water, kneading and extruding to form cylindrical extrudates with a diameter of 1.5 mm and a length between 3 and 5 mm, and calcining the extrudates at 450° C. before use. The extrudates had a Ti concentration of 1.1 wt.-%. The length of the catalyst bed layer was approximately 950 mm.

The reagents were placed in suitable tanks and continuously metered to the reactor by using standard metering pumps. Tank 1 contained chemical grade acetonitrile with a purity of 99.98% (containing 0.01% water, 150 wt.-ppm propionitrile and 1 wt.-ppm acrylonitrile as impurities). Tank 2 contained a standard grade crude, washed hydrogen peroxide solution with a concentration of 40 wt.-% to which 175 wt.-ppm of $(NH_4)H_2PO_4$ were added. Tank 3 contained pressurized liquefied polymer grade propylene. The acetonitrile metering pump was started first at a feed rate of 60.9 g/h, and the reaction temperature was set to 63° C., and the pressure regulator was set to 20 bar. When the reactor had been filled with liquid and the system had been equilibrated, the metering pump for propylene was started at a feed rate of 8.5 g/h. A few minutes later the hydrogen peroxide pump was started at a feed rate of 11.5 g/h (this point in time was defined as t=0). The three streams were mixed at room temperature before they were passed into the reactor. The temperatures measured within the reactor just before and just after the catalytic bed differed by less than 1° C. from the reaction temperature, thus demonstrating that the layer of glass beads was sufficient to heat the reactants to the reaction temperature before they came into contact with the catalyst.

The product stream leaving the reactor was decompressed to ambient pressure into a vessel where gas and liquid phases were separated. The amount of gas was determined volumetrically and its composition analyzed by gas chromatography. The liquid phase was gathered for the entire run (about 300 h) and analyzed. The total concentration of peroxides was determined iodometrically. The concentration of $H_2O_2$ was determined colorimetrically using the titanyl sulfate method. The difference between the two values is generally a good measure for the concentration of hydroperoxypropanols (1-hydroperoxy-2-propanol and 2-hydroperoxy-1-propanol); this was confirmed by determining the amount of propylene glycol by GC before and after reducing the mixture with excess triphenylphosphine). All other organic components were determined by GC using a FID detector. With the exception of acetonitrile, for which only the area-% is given, all other components were determined quantitatively using 1,4-dioxane as an internal standard. The composition of the liquid reactor output is given in Table 1 below.

TABLE 1

| Component | Concentration |
|---|---|
| acetonitrile | 87.5 (area %) |
| water | not measured |
| acetic aldehyde | trace amounts detected in GC |
| propylene oxide | 8.49 wt.-% |
| propionitrile | 0.023 wt.-% |
| hydroxyacetone | b) |
| 1,2-propylene glykol | 0.052 wt.-% |
| dipropylene glykols | trace amounts detected in GC as a mixture of 3 isomers |
| hydroperoxypropanols | 0.27 wt.-% |
| $H_2O_2$ | 0.08 wt.-% |

The liquid stream obtained in the previous step was submitted to distillation in a rotary evaporator with a bath temperature and a pressure of 200 mbar until the concentration of propylene oxide in the residue was below 1 wt.-%.

The residue obtained was analyzed as above, with the difference that all non-peroxidic organic components were determined by quantitative GC with 1,4-dioxane as the internal standard. Water was determined using the Carl-Fischer method. The composition of the residue stream is given in Table 2 below.

TABLE 2

| Component | Concentration/wt-% |
|---|---|
| acetonitrile | 83.8 |
| water | 14.7 |
| acetic aldehyde | 0.02 |
| propylene oxide | 0.7 |
| propionitrile | 0.024 |
| hydroxyacetone | 0.012 |
| 1,2-propylene glycol | 0.12 |
| dipropylene glycols $^{d)}$ (mixture of 3 isomers) | 0.02 |
| hydroperoxypropanols | 0.4 |
| $H_2O_2$ | 0.2 |

This stream was used as feed stream S1 for the process according to Example 2 below.

Example 2

Workup of the Stream Obtained According to Example 1

50 g of mixture as described in Table 2 was introduced into an evacuated, tempered autoclave (volume: 315 ml) equipped with two opposite sapphire windows. After equilibration, 40 g of propene (polymer grade, containing 0.1 wt-% of propane) were introduced into the autoclave. The temperature was held constant at 40° C. The measured pressure was 14.3 bar.

The content of the autoclave was thoroughly mixed by a magnetic stirrer. After the stirrer had been stopped, the mixture immediately separated into two liquid phases. The lower aqueous phase was removed through an outlet at the bottom of the autoclaved and weighed. The aqueous phase weighed 6.12 g, corresponding to 6.8% of the total contents of the autoclave (90 g). Both the aqueous and the organic phase were analysed as described above, and the composition of both phases is given in Table 3 below. As can be seen from the results in Table 3, the ratio of acetonitrile to water (12.1:1) is much lower than the weight ratio in the acetonitrile/water azeotrope (5.7:1) obtainable by simple distillation.

TABLE 3

| Component (wt-%) | Aqueous phase | Organic phase |
|---|---|---|
| C3 (propane + propene) | 1.3 | 42.8 |
| acetonitrile | 24.8 | 52.1 |
| water | 71.2 | 4.3 |
| acetic aldehyde | 0.04 | 0.009 |
| propylene oxide | 0.1 | 0.46 |
| propionitrile | 0.03 | 0.014 |
| hydroxyacetone | 0.04 | 0.005 |
| 1,2-propylene glycol | 0.48 | 0.042 |
| dipropylene glycols | 0.02 | 0.013 |
| hydroperoxypropanols | 1.4 | 0.14 |
| $H_2O_2$ | 0.63 | 0.06 |

Example 3

Separation of Acetonitrile from Water

In a second experiment, again, an amount of 50 g of the stream obtained according to Example 1 was introduced into an evacuated and tempered autoclave, as described in Example 2. Subsequently, 50 g of propene (chemical grade, containing 0.1 wt-% of propane) were introduced into the autoclave. The temperature was held constant at 40° C., the measured pressure was 14.8 bar.

The content of the autoclave was thoroughly mixed by a magnetic stirrer. After the stirrer was stopped, the mixture immediately separated into two liquid phases. The lower aqueous phase was removed through an outlet at the bottom of the autoclaved and weighed. The aqueous phase weighed 6.8 g, corresponding to 6.8% of the total contents of the autoclave (100 g). Both the aqueous and the organic phase were analysed as described above, and the composition of both phases is given in Table 4 below. As can be seen from the results in Table 4, the ratio of acetonitrile to water (13.9:1) is again much lower than the weight ratio in the acetonitrile/water azeotrope (5.7:1) obtainable by simple distillation.

TABLE 4

| Component (wt-%) | Aqueous phase | Organic phase |
|---|---|---|
| C3 (propane + propene) | 1.0 | 53.2 |
| acetonitrile | 23.1 | 43.1 |
| water | 73.1 | 3.1 |
| acetic aldehyde | 0.05 | 0.006 |
| propylene oxide | 0.07 | 0.4 |
| propionitrile | 0.03 | 0.01 |
| hydroxyacetone | 0.04 | 0.004 |
| 1,2-propylene glycol | 0.5 | 0.03 |
| dipropylene glycols | 0.04 | 0.009 |
| hydroperoxypropanols | 1.4 | 0.1 |
| $H_2O_2$ | 0.5 | 0.05 |

The results in Examples 2 and 3 show that by adding a propene mixture, in particular a propene/propane, to a mixture of water and acetonitrile, the mass ratio of acetonitrile:water can be considerably reduced. The effect of increasing the ratio acetonitrile:water is increased when more propene is used.

Example 4

Separation of Acetonitrile from Water

4.1 Providing Stream S2

Since in the following, an entirely continuously operated process according to the present invention is described, the compositions disclosed in detail are to be understood as mean values determined over the entire continuous process which was carried out for 507 hours.

From a continuously operated process for the preparation of propylene oxide, essentially carried out according to Example 1, using the same starting materials, catalyst, and also comprising the downstream work-up stage of distilling off the propylene oxide, however, said distillation carried being carried in a distillation tower, a stream was obtained with a flow rate of 102 kg/h and having, with respect to the main components, a composition as given in Table 5 below.

TABLE 5

| Component | Concentration/wt-% |
|---|---|
| acetonitrile | 78.0 |
| water | 21.5 |

This stream was used as feed stream S1 for the separation process according to invention.

Before stream S1 was passed to the separation device, it was combined with 3 other streams:

The first stream 1 was a stream of (fresh) chemical grade propene (about 95 wt.-% propene, about 5 wt.-% propane) (flow rate of stream 1: 11.4 kg/h).

The second stream 2 was a stream having a propene content of about 95 wt.-%, obtained from a downstream work-up stage as described hereinunder. Said stream 2 corresponds to stream TL1 as discussed in the context of the present invention. Together with stream 1, stream 2 formed stream P as discussed in the context of the present invention. (Flow rate of stream 2: 50 kg/h).

The third stream 3 was a stream which essentially consisted of acetonitrile and water (70.5 wt.-% acetonitrile, 29.3 wt.-% water), obtained from a downstream work-up stage as described hereinunder. Said stream 3 corresponds to stream TL2 as discussed in the context of the present invention. (Flow rate of stream 3: 6.4 kg/h).

Together with said streams 1, 2, and 3, stream S1 formed stream S2 having a flow rate of 169.6 kg/h and having, with respect to the main components, a composition as given in Table 6 below.

TABLE 6

| Component | Concentration/wt-% |
|---|---|
| acetonitrile | 49.5 |
| water | 13.9 |
| propene | 34.5 |

This stream was fed in the separation device, a horizontal gravity settler with a capacity of 2 L.

4.2 Separation According to the Invention

In the horizontal gravity settler, phase separation was achieved at a temperature in the range of from 30 to 40° C. and at a pressure of 18 bar. The obtained upper layer was fed as a stream with a flow rate of 148 kg/h to a distillation column A, the obtained lower phase as a stream with a flow rate of 21.6 kg/h to a distillation column B1. The upper layer had a composition, with respect to the main components, as given in Table 7 below:

TABLE 7

| Component | Concentration/wt-% |
|---|---|
| acetonitrile | 53.8 |
| water | 4.5 |
| propene | 39.5 |

The lower layer had a composition, with respect to the main components, as given in Table 8 below:

TABLE 8

| Component | Concentration/wt-% |
|---|---|
| acetonitrile | 20.4 |
| water | 78.3 |

4.3 Work-Up of the Upper Layer

The stream obtained as upper layer from the phase separation device was passed, as mentioned, to a distillation column A.

Distillation column A was configured as bubble-tray column (internal diameter: 200 mm; length: 10000 mm) made of stainless steel of quality 1.4541, 40 trays and integrated bottom reboiler. Column A was operated at a pressure of 18 bar and a bottom temperature of 105-107° C. The reflux ratio of column A was 0.2.

The top stream obtained from column A at a temperature at the top of the column in the range of from 44-45° C. and having a propene content of 95 wt.-%, was recycled with a flow rate of 50 kg/h as starting material to the continuously operated epoxidation reaction.

The bottoms stream obtained from column A, having a composition, with respect to the main components, according Table 9

TABLE 9

| Component | Concentration/wt-% |
|---|---|
| acetonitrile | 81.2 |
| water | 6.8 |
| propene | 11.2 | was recycled into the separation device as stream 2 to be admixed with stream S1 and streams 1 and 3 to obtain stream S2.

4.4 Work-Up of the Lower Layer

The stream obtained as lower layer from the phase separation device was passed, as mentioned, to a distillation column B1.

Distillation column B1 was configured as bubble-tray column (internal diameter: 100 mm; length: 9500 mm) made of stainless steel of quality 1.4541, 50 trays and integrated bottom reboiler. Column A was operated at a top pressure of 14 bar and a bottom temperature of 190-196° C. The reflux ratio of column B1 was 1.0.

The bottoms stream obtained from distillation column B1 with a flow rate of 11.6 kg/h had a water content of 97.1 wt.-% and further contained non-specified high boilers. The acetonitrile content of the bottoms stream was less than 0.1 wt.-%.

The top stream obtained from column B1 at a temperature at the top of the column in the range of from 176-185° C. had a composition, with respect to the main components, according Table 10

TABLE 10

| Component | Concentration/wt-% |
|---|---|
| acetonitrile | 45.0 |
| water | 55.0 | i.e. essentially the composition of the acetonitrile/water azeotrope. This top stream of column B1 was fed with a flow rate of 10.0 kg/h to a downstream distillation column B2.

Distillation column B2 was configured as packed column (DN80*9500) (DN 80=Diameter Nominal 80 according to standard EN 10255; length=9500 mm) made of stainless steel of quality 1.4541 with integrated bottom reboiler. Column B2 was operated at a top pressure of 1.5 bar and a bottom temperature of 111-112° C. As packing material, Kühni Rombopak® 9m was used (height of the packing: 6500 mm). The reflux ratio of column B2 was 0.7.

The bottoms stream having a flow rate of 3.6 kg/h had a water content of 99.9 wt.-%.

The top stream obtained from column B2 at a temperature at the top of the column in the range of from 74-85° C. had a composition, with respect to the main components, according Table 11

TABLE 11

| Component | Concentration/wt-% |
|---|---|
| acetonitrile | 70.5 |
| water | 29.3 |

This top stream of column B2 was recycled with a flow rate of 6.4 kg/h into the separation device as stream 3 to be admixed with stream S1 and streams 1 and 2 to obtain stream S2.

SUMMARY

The major advantage of the inventive process of separating acetonitrile from water is particularly evident in case the separated acetonitrile is recycled as starting material of an highly integrated process for the epoxidation of propene, in particular with aqueous hydrogen peroxide. In such integrated process, the inventive process allows for big savings in energy while at the same time a ratio of acetonitrile:water can be achieved which is higher than the ratio of acetonitrile:water achievable by simple distillation at ambient pressure. Presently, without wanting to be bound to any theory, it is believed that in order to separate and recycle acetonitrile from the reaction mixture obtained from such epoxidation reaction or a suitable mixture obtained from one or more work-up stages by distillation at ambient pressure, all the acetonitrile plus the amount of water contained in the azeotrope would have to be evaporated. However, if a lower amount of water in the acetonitrile is desired, then a two-pressure distillation set-up would be needed, but this would imply that the complete amount of acetonitrile would have to be evaporated twice, necessarily leading to a large energy consumption. Thus, using the method of the present invention, only a fraction of the energy is needed when compared to the above mentioned method due to our finding that the liquid/liquid separation required very little energy. Further, it was possible to design the desired separation apparatus in the form a comparatively simple setup. The only significant contribution to the energy consumption is needed to recover the low amount of acetonitrile present in the aqueous phase after the phase separation. The present invention clearly offers a big advantage, both from the point of view of energy consumption and from the point of view of required investment.

Example 4 further clearly illustrates a highly integrated embodiment of the separation process of the present invention wherein downstream of the separation process, the layers obtained from the separation device are recycled to the process, either to the separation process or to the upstream epoxidation process, to a maximum extent, thus providing a highly desirable process setup, both from an economical and an ecological point of view.

In particular, the present invention relates to the following embodiments, including the specific combinations of these embodiments resulting from the back-references in the individual embodiments, as indicated:

1. A method for separating acetonitrile from water, comprising
   (i) providing a stream S1 containing at least 95 wt.-%, based on the total weight of S1, acetonitrile and water, wherein the weight ratio of acetonitrile:water is greater than 1;
   (ii) adding a stream P, comprising at least 95 wt.-% C3, based on the total weight of stream P, to S1 to obtain a mixed stream S2, C3 being propene optionally admixed with propane with a minimum weight ratio of propene:propane of 7:3;
   (iii) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrile wherein the weight ratio of acetonitrile:water in L2 is less than 1;
   (iv) separating L1 from L2.
2. The method of embodiment 1, wherein in (ii), a liquid stream P is added to a liquid stream S1.
3. The method of embodiment 1 or 2, wherein S1 contains from 60 to 85 wt.-%, preferably from 65 to 80 wt.-% acetonitrile, and from 10 to 35 wt.-%, preferably from 15 to 30 wt.-% water, in each case based on the total weight of S1.
4. The method of any of embodiments 1 to 3, wherein in (ii), P is added to S1 in an amount so that the weight ratio of C3:acetonitrile in S2 is in the range of from 0.2:1 to 5:1, preferably from 0.5:1 to 2:1.
5. The method of any of embodiments 1 to 4, wherein in (iii), S2 is subjected to a temperature of from 5 to 90° C., in particular from 25 to 45° C., and to a pressure in the range of from 15 to 50 bar, in particular from 15 to 25 bar.
6. The method of any of embodiments 1 to 5, wherein at least one liquid phase separation improving agent is added to S1 in (i) and/or to S2 in (ii), preferably in an amount of 1 wt.-% at most, based on the total weight of S1 and/or S2.
7. The method of any of embodiments 1 to 6, wherein in (iv), L1 is separated from L2 in a gravity settler, preferably in a horizontal gravity settler.
8. The method of any of embodiments 1 to 7, wherein at least 95 wt.-%, preferably at least 98 wt.-% of L1 consist of C3, acetonitrile and water, the water content of L1 being less than 10 wt.-%, preferably in the range of from 1 to 5 wt.-%, based on the total weight of L1.
9. The method of any of embodiments 1 to 8, wherein at least 95 wt.-%, preferably at least 98 wt.-% of L2 consist of C3, acetonitrile and water, the C3 content of L2 being 5 wt.-% at most, based on the total weight of L2, and the acetonitrile content of L2 being less than 45 wt.-%, preferably in the range of from 10 to 35 wt.%, based on the total weight of L2.

10. The method of any of embodiments 1 to 9, further comprising subjecting L1 to a distillation stage wherefrom a stream TL1 is obtained which contains at least 90 wt.-%, preferably at least 95 wt.-% C3, based on the total weight of TL1.
11. The method of embodiment 10, wherein, from said distillation stage, a further stream BL1 is obtained, at least 95 wt.-%, preferably at least 98 wt.-% of BL1 consisting of C3, acetonitrile and water, wherein the C3 content of BL1 is in the range of from 7 to 18 wt.-%, preferably from 10 to 15 wt.-%, in each case based on the total weight of BL1.
12. The method of embodiment 10 or 11, wherein in said distillation stage, one distillation tower is employed and wherein said distillation is carried out at a dew-point at the top of said distillation tower of at least 40° C., preferably in the range of from 40 to 80° C.
13. The method of any of embodiments 10 to 12, wherein at least a portion of TL1 is recycled into (ii).
14. The method of any of embodiments 1 to 13, further comprising subjecting L2 to a distillation stage wherefrom a stream TL2 is obtained which contains from 75 to 95 wt.-%, preferably from 80 to 85 wt.-% acetonitrile, based on the total weight of TL2.
15. The method of embodiment 14, wherein at least a portion of TL2 is recycled into (ii).
16. The method of embodiment 14 or 15, wherein said distillation stage is a two pressure distillation process, wherein in a first distillation tower, distillation is carried out at a top pressure which is higher than the top pressure of a second distillation tower and wherein the condenser used to condense the top stream of the first distillation tower is used simultaneously as the vaporizer of the second distillation tower.
17. The method of embodiment 16, wherein
    (aa) L2 is introduced into the first distillation tower from which a vapor top stream VTL2 is obtained containing from 50 to 70 wt.-% acetonitrile, based on the total weight of top stream VTL2, the distillation preferably being carried out at a top pressure of from 10 to 20 bar; and
    (bb) at least partially condensing VTL2 obtained in (aa) and introducing the condensed stream into the second distillation tower wherefrom TL2 is obtained as top stream, the distillation preferably being carried out at a top pressure of from 1 to 5 bar,
    wherein the condenser used to condense VTL2 is simultaneously used as vaporizer of the second distillation tower.
18. The method of any of embodiments 1 to 17, wherein according to (i), S1 is provided by a process comprising
    (a) reacting propene, optionally admixed with propane, with hydrogen peroxide in a reaction apparatus in the presence of acetonitrile as solvent, obtaining a stream S0 leaving the reaction apparatus, S0 containing acetonitrile, water, propylene oxide, and optionally non-reacted propene, oxygen, and further optionally propane;
    (b) optionally separating propene, oxygen, and propane from S0 to obtain a stream essentially consisting of acetonitrile, water, and propylene oxide;
    (c) separating propylene oxide from S0 or the stream obtained from (b), thus obtaining stream S1.
19. The method of embodiment 18, wherein in (a), propene is reacted with hydrogen peroxide in the presence of a heterogeneous catalyst, said catalyst preferably comprising a zeolite, preferably a titanium zeolite, more preferably a titanium zeolite of the structure type MWW.
20. The method of embodiment 18 or 19, wherein in (b), a distillation tower is used and at the top of said distillation tower, acetonitrile, optionally admixed with water, is added as a stripping agent.
21. The method of any of embodiments 18 to 20, wherein at least a portion of stream BL1 according to embodiment 11 is recycled into (a).
22. The method of any of embodiments 18 to 21, wherein prior to (ii), S1 is subjected to a hydrogenation stage, the resulting hydrogenated stream optionally being subjected to a distillation stage.
23. The method of any of embodiments 1 to 22, wherein S1 additionally contains at least one glycol, preferably in an amount of 1 wt.-% or less, based on the total weight of S1.
24. The method of embodiment 23, wherein the at least one glycol is selected from the group consisting of propylene glycol, dipropylene glycol, tripropylene glycol, and a mixture of two or three thereof.
25. The method of embodiment 23 or 24, the bottoms stream obtained from the first distillation tower according to embodiment 16 or 17 containing at least a portion of the at least one glycol, wherein said bottoms stream, optionally after combining with the bottoms stream obtained from the second distillation tower according to embodiment 18 or 19, is subjected to a glycol separation stage.
26. A highly integrated process for the preparation of propylene oxide, the process comprising
    (a) reacting propene, optionally admixed with propane, with hydrogen peroxide in a reaction apparatus in the presence of acetonitrile as solvent, obtaining a stream S0 leaving said reaction apparatus, S0 containing acetonitrile, water, propylene oxide, and optionally non-reacted propene, oxygen, and optionally propane;
    (b) optionally separating propene, optionally together with propane, and oxygen from S0 to obtain a stream, at least 99 wt.-% thereof consisting of acetonitrile, water, and propylene oxide;
    (c) separating propylene oxide from S0 or the stream obtained from (b), thus obtaining a stream S1 containing at least 95 wt.-% acetonitrile and water, based on the total weight of S1, wherein the weight ratio of acetonitrile:water is greater than 1;
    (d) adding a stream P, comprising at least 95 wt.-% C3, based on the total weight of stream P, to S1 to obtain a mixed stream S2, C3 being propene optionally admixed with propane with a minimum weight ratio of propene:propane of 7:3;
    (e) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrile wherein the weight ratio of acetonitrile:water in L2 is less than 1;
    (f) separating L1 from L2;
    (g) subjecting L1 to a distillation stage wherefrom a stream TL1 is obtained which contains at least 90 wt.-% C3, based on the total weight of TL1; and wherefrom a further stream BL1 is obtained, at least 95 wt.-% of BL1 consisting of C3, acetonitrile and water, wherein the C3 content of BL1 is in the range of from 7 to 18 wt.-% based on the total weight of BL1;
    (h) subjecting L2 to a distillation stage wherefrom a stream TL2 is obtained which contains from 75 to 95 wt.-%, preferably from 80 to 85 wt.-% acetonitrile, based on the total weight of TL2;

wherein at least a portion of stream BL1 is recycled into (a); and/or
wherein at least a portion of TL1 is recycled into (d); and/or
wherein at least a portion of TL2 is recycled into (d).

27. The process of embodiment 26, wherein BL1 is recycled into (a) and TL1 is recycled into (d) and TL2 is recycled into (d).

28. The process of embodiment 26 or 27, further comprising
(y) subjecting the stream obtained from (c) to a hydrogenation stage;
(z) subjecting the stream obtained from (y) to a distillation stage to obtained stream S1 and subjecting S1 to (d).

The invention claimed is:

1. A method for separating acetonitrile from water, comprising
(i) providing a stream S1 comprising at least 95 wt.-%, based on the total weight of S1, acetonitrile and water, wherein the weight ratio of acetonitrile : water is greater than 1;
(ii) adding a stream P, comprising at least 95 wt.-% C3, based on the total weight of stream P, to S1 to obtain a mixed stream S2, C3 being propene optionally admixed with propane with a minimum weight ratio of propene : propane of 7:3;
(iii) subjecting S2 to a temperature of 92° C. at most and a pressure of at least 10 bar, obtaining a first liquid phase L1 essentially consisting of C3, acetonitrile, and water, and a second liquid phase L2 essentially consisting of water and acetonitrile wherein the weight ratio of acetonitrile: water in L2 is less than 1;
(iv) separating L1 from L2.

2. The method of claim 1, wherein in (ii), a liquid stream P is added to a liquid stream S1.

3. The method of claim 1, wherein S1 comprises from 60 to 85 wt.-% acetonitrile, and from 10 to 35 wt.-% water, in each case based on the total weight of S1.

4. The method of claim 1, wherein in (ii), P is added to S1 in an amount so that the weight ratio of C3: acetonitrile in S2 is in the range of from 0.2:1 to 5:1.

5. The method of claim 1, wherein in (iii), S2 is subjected to a temperature of from 5 to 90° C., and to a pressure in the range of from 15 to 50 bar.

6. The method of claim 1, wherein at least one liquid phase separation improving agent is added to S1 in (i) and/or to S2 in (ii).

7. The method of claim 1, wherein in (iv), L1 is separated from L2 in a gravity settler.

8. The method of claim 1, wherein at least 95 wt.-% of L1 consist of C3, acetonitrile and water, the water content of L1 being less than 10 wt.-%, based on the total weight of L1.

9. The method of claim 1, wherein at least 95 wt.-%-of L2 consist of C3, acetonitrile and water, the C3 content of L2 being 5 wt.-% at most, based on the total weight of L2, and the acetonitrile content of L2 being less than 45 wt.-%, based on the total weight of L2.

10. The method of claim 1, further comprising subjecting L1 to a distillation stage wherefrom a stream TL1 is obtained which contains at least 90 wt.-% C3, based on the total weight of TL1.

11. The method of claim 10, wherein, from said distillation stage, a further stream BL1 is obtained, at least 95 wt.-% of BL1 consisting of C3, acetonitrile and water, wherein the C3 content of BL1 is in the range of from 7 to 18 wt.-%, in each case based on the total weight of BL1.

12. The method of claim 10, wherein in said distillation stage, one distillation tower is employed and wherein said distillation is carried out at a dew-point at the top of said distillation tower of at least 40° C.

13. The method of claim 10, wherein at least a portion of TL1 is recycled into (ii).

14. The method of claim 1, further comprising subjecting L2 to a distillation stage wherefrom a stream TL2 is obtained which contains from 75 to 95 wt.-% acetonitrile, based on the total weight of TL2.

15. The method of claim 14, wherein at least a portion of TL2 is recycled into (ii).

16. The method of claim 14, wherein said distillation stage is a two pressure distillation process, wherein in a first distillation tower, distillation is carried out at a top pressure which is higher than the top pressure of a second distillation tower and wherein the condenser used to condense the top stream of the first distillation tower is used simultaneously as the vaporizer of the second distillation tower.

17. The method of claim 16, wherein
(aa) L2 is introduced into the first distillation tower from which a vapor top stream VTL2 is obtained containing from 50 to 70 wt.-% acetonitrile, based on the total weight of top stream VTL2, the distillation preferably being carried out at a top pressure of from 10 to 20 bar; and
(bb) at least partially condensing VTL2 obtained in (aa) and introducing the condensed stream into the second distillation tower wherefrom TL2 is obtained as top stream,
wherein the condenser used to condense VTL2 is simultaneously used as vaporizer of the second distillation tower.

18. The method of claim 1, wherein according to (i), S1 is provided by a process comprising
(a) reacting propene, optionally admixed with propane, with hydrogen peroxide in a reaction apparatus in the presence of acetonitrile as solvent, obtaining a stream S0 leaving the reaction apparatus, S0 containing acetonitrile, water, propylene oxide, and optionally non-reacted propene, oxygen, and further optionally propane;
(b) optionally separating propene, oxygen, and propane from S0 to obtain a stream essentially consisting of acetonitrile, water, and propylene oxide;
(c) separating propylene oxide from S0 or the stream obtained from (b), thus obtaining stream S1.

19. The method of claim 18, wherein in (a), propene is reacted with hydrogen peroxide in the presence of a heterogeneous catalyst, said catalyst preferably comprising a zeolite, preferably a titanium zeolite, more preferably a titanium zeolite of the structure type MWW.

20. The method of claim 18, wherein in (b), a distillation tower is used and at the top of said distillation tower, acetonitrile, optionally admixed with water, is added as a stripping agent.

21. The method of claim 18, wherein at least a portion of stream BL1 according to claim 11 is recycled into (a).

22. The method of claim 18, wherein prior to (ii), S1 is subjected to a hydrogenation stage, the resulting hydrogenated stream optionally being subjected to a distillation stage.

23. The method of claim 1, wherein S1 additionally comprises at least one glycol.

24. The method of claim 23, wherein the at least one glycol is selected from the group consisting of propylene glycol, dipropylene glycol, tripropylene glycol, and a mixture of two or three thereof.

25. The method of claim 1, wherein S1 comprises from 65 to 80 wt.-% acetonitrile and from 15 to 30 wt.-% water, in each case based on the total weight of S1.

26. The method of claim 1, wherein in (ii), P is added to S1 in an amount so that the weight ratio of C3: acetonitrile in S2 is in the range of from 0.5:1 to 2:1.

27. The method of claim 1, wherein in (iii), S2 is subjected to a temperature of from 25 to 45° C., and to a pressure in the range of from 15 to 25 bar.

28. The method of claim 1, wherein at least one liquid phase separation improving agent is added to S1 in (i) and/or to S2 in (ii) in an amount of 1 wt.-% at most, based on the total weight of S1 and/or S2.

29. The method of claim 1, wherein in (iv), L1 is separated from L2 in a horizontal gravity settler.

30. The method of claim 1, wherein at least 98 wt.-% of L1 consist of C3, acetonitrile and water, the water content of L1 being in the range of from 1 to 5 wt.-%, based on the total weight of L1.

31. The method of claim 1, wherein at least 98 wt.-% of L2 consist of C3, acetonitrile and water, the C3 content of L2 being 5 wt.-% at most, based on the total weight of L2, and the acetonitrile content of L2 being in the range of from 10 to 35 wt.-%, based on the total weight of L2.

32. The method of claim 1, further comprising subjecting L1 to a distillation stage wherefrom a stream TL1 is obtained which contains at least 95 wt.-% C3, based on the total weight of TL1.

33. The method of claim 10, wherein, from said distillation stage, a further stream BL1 is obtained, at least 98 wt.-% of BL1 consisting of C3, acetonitrile and water, wherein the C3 content of BL1 is in the range of from 10 to 15 wt.-%, in each case based on the total weight of BL1.

34. The method of claim 10, wherein in said distillation stage, one distillation tower is employed and wherein said distillation is carried out at a dew-point at the top of said distillation tower in the range of from 40 to 80° C.

35. The method of claim 1, further comprising subjecting L2 to a distillation stage wherefrom a stream TL2 is obtained which contains from 80 to 85 wt.-% acetonitrile, based on the total weight of TL2.

36. The method of claim 17, wherein in (bb) said distillation is carried out at a top pressure of from 1 to 5 bar.

37. The method of claim 23, wherein S1 additionally comprises at least one glycol in an amount of 1 wt.-% or less, based on the total weight of S1.

* * * * *